(12) United States Patent
Gusev

(10) Patent No.: US 8,446,587 B2
(45) Date of Patent: *May 21, 2013

(54) FLASH PHOTOLYSIS SYSTEM

(76) Inventor: Alex Gusev, Sarasota, FL (US)

( * ) Notice: Subject to any disclaimer, the term of this patent is extended or adjusted under 35 U.S.C. 154(b) by 21 days.

This patent is subject to a terminal disclaimer.

(21) Appl. No.: 13/210,632

(22) Filed: Aug. 16, 2011

(65) Prior Publication Data

US 2013/0045136 A1 Feb. 21, 2013

(51) Int. Cl.
*G01N 21/00* (2006.01)
(52) U.S. Cl.
USPC .......................................... 356/432
(58) Field of Classification Search
USPC ........................................ 356/432, 445, 447
See application file for complete search history.

(56) References Cited

U.S. PATENT DOCUMENTS

| | | | |
|---|---|---|---|
| 5,706,094 A | 1/1998 | Maris | |
| 7,106,971 B1 | 9/2006 | Davis | |
| 7,817,270 B2 * | 10/2010 | Gusev | 356/318 |
| 2001/0028460 A1 * | 10/2001 | Maris et al. | 356/432 |
| 2003/0055342 A1 | 3/2003 | Toida | |
| 2005/0036150 A1 | 2/2005 | Izatt et al. | |
| 2006/0256916 A1 * | 11/2006 | Kotelyanskii et al. | 378/71 |
| 2008/0186486 A1 | 8/2008 | Gusev | |
| 2008/0251740 A1 | 10/2008 | Dilhaire et al. | |
| 2012/0113417 A1 * | 5/2012 | Linfield et al. | 356/300 |

* cited by examiner

*Primary Examiner* — Roy M Punnoose
(74) *Attorney, Agent, or Firm* — Fraser Clemens Martin & Miller LLC; J. Douglas Miller

(57) ABSTRACT

A pump-probe LFP system is adapted to a substantially lower energy requirement of a pump light source and a probe light source. The LFP system includes a photonic crystal fiber based probe light source, a pump light source adapted to produce light pulses with nanojoule or higher energy, a main laser source to generate a first beam portion to the probe light source and a second beam portion to the pump light source, a delay generator, computer, an optical modulator, and a detector.

8 Claims, 2 Drawing Sheets

FLASH PHOTOLYSIS SYSTEM

FLASH PHOTOLYSIS SYSTEM

FIELD OF THE INVENTION

The present invention relates to the field of laser flash photolysis and more particularly to a flash photolysis system with improved performance over existing flash photolysis spectrometers.

BACKGROUND OF THE INVENTION

Laser flash photolysis (LFP) is a technique utilized to study reaction mechanisms in chemical and biological processes. The technique was introduced in 1966 by Lindqvist at the CNRS in France and the technique was quickly developed by various research groups around the world. LFP was brought about by the invention of the laser in the early 1960s. The technique of LFP consists of a pulsed laser source that generates a chemical species in a sample to be studied, an optical and electronic system capable of sensing optical changes in a sample, and a computer suitably equipped to selectively capture, process, and display the data. The optical and electronic systems constitute a fast spectrometer capable of acquiring spectra of short-lived chemical species called "intermediates". The optical and electronic systems then record the evolution of the intermediates over time. The time resolution in such fast spectrometer can be achieved by two primary methods.

A first method includes use of fast electronics where a readout of a fast detector is digitized and recorded in real time, or when an electronic gating is applied to the detector. The electronic gating is typically used with array-based spectrometers where the output cannot be processed rapidly enough to perform real time data acquisition. Both techniques typically utilize continuous wave (CW) or pulsed xenon arc lamps as a probe light source. Due to the low intrinsic brightness and poor collimation of a probe beam produced by the probe light source, an optical overlap between the probe and a pump (excitation) beam takes place over an area of approximately 1 $cm^2$, thereby placing energy requirements on the laser pulse necessary to induce chemical changes in the sample. The corresponding pump laser pulses typically have energy of a few millijoules. Because of the pulse energy requirement, only a limited number of lasers, known as Q-switched lasers, can be used with the xenon arc lamp probe light source to produce the required energy.

A second method is called optical gating or the "pump-probe" method. In this method, the dynamics of a chemical change of a sample is monitored by studying a series of light pulses from a laser at different times as the light pulses (pump beam) are passed through the sample. The probe and pump beams travel through the same volume of the sample studied. A pulse of the pump beam induces a transient chemical change in the sample which affects the optical properties of the sample. A spectrum of a pulse of the probe beam passing through the sample is altered by the changes made to the sample by the pump beam depending on when the probe pulse arrives at the sample with respect to the pump pulse.

Where the probe beam travels in front of the pump beam, the probe beam will only measure the sample before the excitation event. As the probe beam is delayed, it arrives at the sample simultaneously with the pump pulse, corresponding to a time zero. The delay of the probe beam is incrementally increased over a desired time interval. The corresponding changes in the probe beam monitored by a detector are therefore assigned to particular delays (time) after the excitation event. A series of probe beams at various delays represents information about the dynamics of the changes in the sample caused by the pump beam.

At each of the delays of the probe beam, two spectra of the probe beam are recorded by the detector. A first spectrum corresponds to the probe beam traveling through the sample together with the pump beam. A second spectrum, a reference spectrum, corresponds to the probe beam sent through the sample without the pump beam. Usually at a particular pump probe delay, a series of such probe spectrum pairs are averaged in order to obtain a sufficient signal to noise ratio. The pump beam energy in such experimental setups is often limited to several microjoules. Therefore, in order to achieve comparable instrument sensitivity and similar photon flux in the excitation beam, the pump beam and the probe beam are spatially overlapped in the sample over an area less than 1 $mm^2$. Generation of a probe beam that can satisfy the above requirement is possible only if a highly collimated beam such as a laser is used.

Optical gating has been successfully used with femtosecond and picosecond lasers. The femtosecond or picosecond laser output is split into several parts, one of which is used to produce a probe beam with desired wavelength specifications, usually through super-continuum generation or optical parametric amplification. The materials used for super-continuum generation are typically bulk materials—crystals such as sapphire, calcium fluoride, etc. or liquids such as water, etc. The resulting beam is then used to probe the photo-induced changes in the sample. The time resolution is realized by varying the travel path length of the probe beam with respect to the pump beam, which allows for extremely high temporal resolution, down to several femtoseconds. However, in order to generate a super-continuum in bulk materials such as sapphire one needs to have laser pulses with high peak power (MegaW), which can be produced by only a limited number of lasers including amplified femtosecond lasers. Such amplified femtosecond lasers are expensive and have a large footprint (8-10 $ft^2$).

Commonly owned U.S. Pat. No. 7,817,270 B2 shows a nanosecond pump-probe LFP system that is adapted to a substantially lower energy requirement of a pump light source and a probe light source. The LFP system includes a photonic crystal fiber based probe light source, a pump light source adapted to produce light pulses with nanojoule or higher energy, a delay generator, a computer, and a detector.

SUMMARY OF THE INVENTION

A LFP system for performing laser flash photolysis have been surprisingly developed and are adapted to substantially lower the energy requirement of a pump and probe light source. The LFP system includes a probe light source, a pump light source adapted to produce light pulses with nanojoule or higher level energy, a delay generator, an optical modulator, and a detector.

In the system for flash photolysis a main laser source generates a beam of light and a beam splitter generates a first portion beam and a second portion beam from the beam of light. The probe light source is responsive to the first portion beam for generating a first pulsed beam of light to travel through a sample in a flash photolysis application, wherein the probe light source is a laser energized photonic crystal fiber. The delay generator is one of an optical delay line or an optical delay generator to regulate a time delay between generation of the first pulsed beam and generation of the second pulsed beam throughout the flash photolysis application. The pump light source is responsive to the second portion beam from the delay generator for generating a second pulsed beam of light to travel through the sample and initiate a chemical reaction in the sample. The detector receives the first pulsed beam exiting the sample to detect a change in absorption of the first pulsed beam in the sample caused by the second pulsed beam.

DESCRIPTION OF THE DRAWINGS

The above and other objects and advantages of the invention will become readily apparent to those skilled in the art from reading the following detailed description of the invention when considered in the light of the accompanying figures.

DETAILED DESCRIPTION OF THE INVENTION

Figure 1:
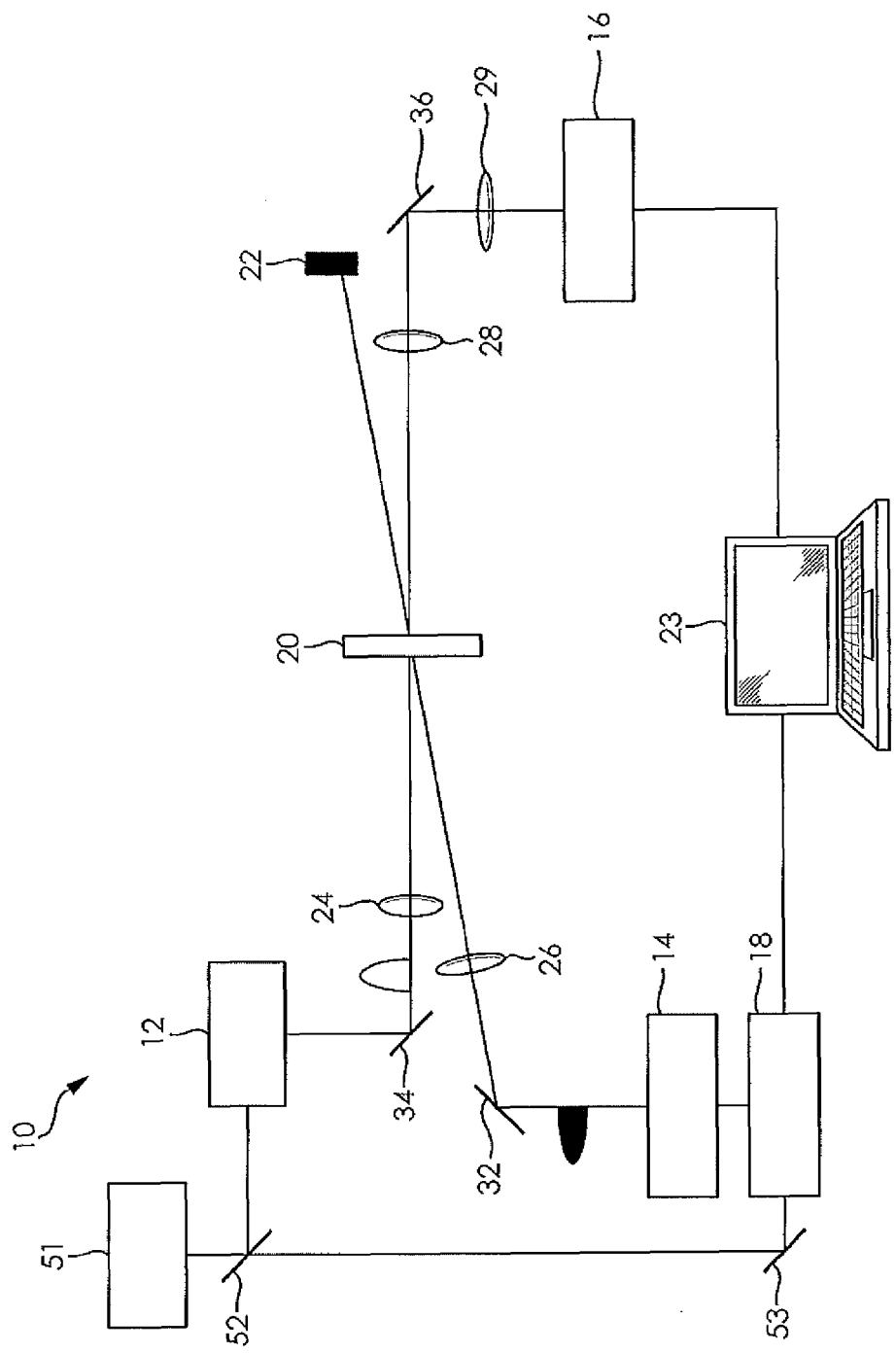
FIG. 1 shows a schematic layout of an LFP system according to an embodiment of the present invention.

The following detailed description and appended drawings describe and illustrate various exemplary embodiments of the invention. The description and drawings serve to enable one skilled in the art to make and use the invention, and are not intended to limit the scope of the invention in any manner. In respect of the methods disclosed, the steps presented are exemplary in nature, and thus, the order of the steps is not necessary or critical.

Referring to the figures, each illustrates an LFP system 10 which includes a probe light source 12, a pump light source 14, a detector 16, and a delay generator 18. The probe light source 12 shown is a photonic crystal fiber pumped by a laser 51. The probe light source 12 is adapted to be focused to areas as small as several square microns. It is understood that the probe light source 12 may be any conventional probe light source that is adapted to be focused to areas as small as several square microns such as a pulsed femtosecond laser oscillator coupled to a photonic fiber, for example.

The pump light source 14 is typically a harmonics generator or an optical parametric oscillator pumped by the laser 51 adapted to produce a collimated beam with an energy level of at least several nanojoules and referred to as an excitation light source. The pump light source 14 may also be an amplified femtosecond laser, a non-amplified femtosecond laser oscillator, a picosecond laser, a Q-switched nanosecond laser, a dye laser, a nitrogen laser, or a nanosecond microchip laser, as desired.

The detector 16 is a broadband detector, such as a CCD based spectrometer adapted to measure a change in the absorption of light by a sample 20. The detector 16 may be further adapted to transmit a measurement signal to a computer 23. It is understood that the detector 16 may be any device adapted to measure the properties of light over a specific portion of the electromagnetic spectrum.

The delay generator 18 is typically an optical delay generator. The delay generator 18 is in electrical communication with the computer 23 and adapted to optically control the time delay between the probe beam produced by the probe light source 12 and the pump beam produced by the pump light source 14. The delay generator 18 is further adapted to selectively vary the delay between the pump beam and the probe beam by any amount, though typical LFP experimentation rarely requires a delay of over 10 nanoseconds. It is understood that the delay generator 18 can be installed before or after the pump light source 14, or before or after the probe light source 12.

The LFP system 10 further includes a beam block 22, a plurality of lens optics 24, 26, 28, 29, a plurality of reflective optics 32, 34, 36, 53, and a beam splitter 52. The beam block 22 is adapted to capture and absorb electromagnetic energy such as, a beam of collimated light.

The lens optics 24, 26, 28, 29 include a first lens 24, a second lens 26, a third lens 28, and a fourth lens 29. The first lens 24 is disposed in the path of the beam produced by the probe light source 12 and is adapted to focus the probe beam into the sample 20. The second lens 26 is disposed in the path of the beam produced by the pump light source 14 and is adapted to focus the pump beam into the sample 20. The third lens 28 and the fourth lens 29 are adapted to collect and guide the beam produced by the probe light source 12 to the detector 16. Although the LFP system 10 is shown having four lens optics 24, 26, 28, 29, it is understood that any number of lens optics may be used, as desired. Alternatively, curved mirrors can be utilized instead of lenses.

The reflective optics 32, 34, 36, 53 may be any conventional reflective optics to direct light beams such as mirrors, for example. The reflective optics 32, 34, 36, 53 are disposed in the path of the beams generated by the probe light source 12 and the pump light source 14 to affect the desired direction of the beams. Although the LFP system 10 is shown as having four reflective optics 32, 34, 36, 53, it is understood that any number of reflective optics may be used to affect the desired direction of the beams.

The beam splitter 52 is disposed in the path of the beam generated by a main laser source 51 to reflect two portions of the main beam in desired directions. The main beam is separated by the splitter 52 into a first beam portion directed to the probe light source 12 and a second beam portion. The embodiment shown in FIG. 1 directs the second beam portion to the pump light source 14. In the embodiment shown in FIG. 2, the second beam portion is first directed to an optical modulator 54. The modulator 54 then provides the second beam portion to the pump light source 14.

In use, the probe light source 12 generates probe beam pulses that are focused into an area of approximately $0.1\ mm^2$ in the sample 20 by the first lens 24 while the pump light source 14 generates pump beam pulses that are focused into the same area of approximately $0.1\ mm^2$ by the second lens 26 and having an energy-level of several nanojoules. The probe and pump beams are therefore caused to spatially overlap in the sample 20. The pump beams are captured by a beam block 22 after passing through the sample 20. The probe beam is collected by the third lens 28 and the fourth lens 29 and guided into the detector 16. Reflective optics 32, 34, 36 are provided to direct the beams from the light sources 12, 14. Changes to the sample 20 and the difference in light absorption of the sample 20 are then measured by the detector 16 and recorded by the computer 23.

The probe beam pulse is produced at a constant frequency of approximately 50 kHz. It is understood any frequency may be used, as desired. The computer 23 controls timing of the pulses from the pump light source 14 through the delay generator 18. The pulses from the pump light source 14 are sent to the sample 20 so that that the pump pulse precedes the probe pulse by a desired time interval, thereby generating a desired pump-probe delay.

The optical modulator 54 is used to modulate the pump pulses from the pump light source 14. The modulator 54 can be an optical chopper, an acousto-optical modulator, an electro-optical modulator, etc. The modulator 54 is controlled by the PC 23. To obtain a spectrum of the probe beam pulse without the pump beam pulse present in the sample 20, a signal is sent to the modulator 54 that blocks the pump pulses at a rate of every other probe beam pulse.

By varying the timing of the probe beam and pulse beam with the delay generator 18, the delay between the pulses available for experimentation on a sample 20 by the LFP system 10 may be varied as desired, though typically the interval for experimentation will be less than ten nanoseconds. Additional benefits of the LFP system 10 include a reduction in the overall size of the LFP system 10 to an area of less than approximately 4-6 ft$^2$ by including optical components such as the lens optics 24, 26, 28, 29 and the reflective optics 32, 34, 36, 53 to direct the beams, thereby minimizing the overall cost of the LFP system 10 as compared to other commercially available LSP systems.

Figure 2:
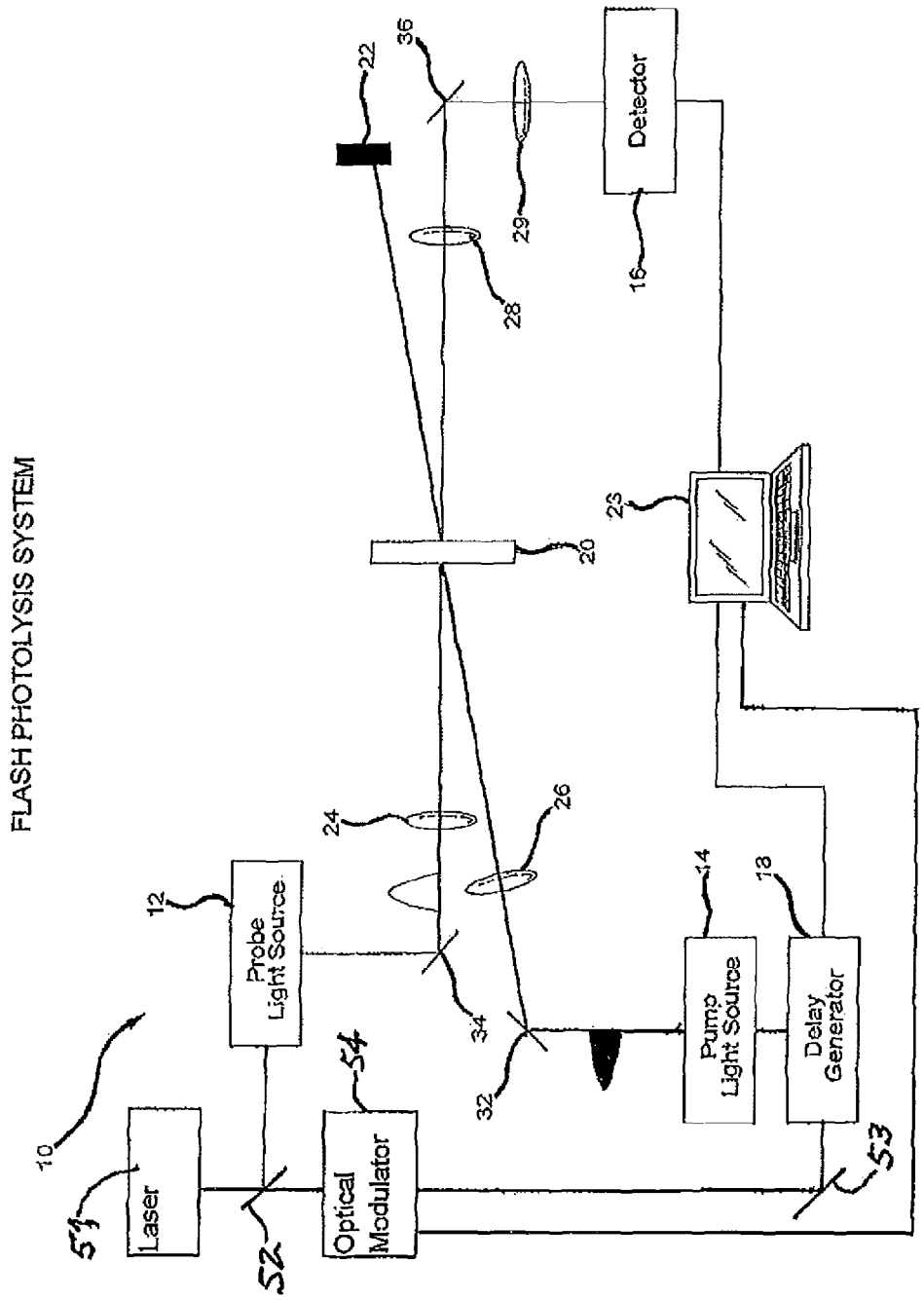
FIG. 2 shows a schematic layout of an LFP system according to another embodiment of the present invention.

The LFP system 10, according to the embodiment of the invention shown in FIG. 2, includes the main laser source 51, the probe light source 12, the pump light source 14, the detector 16, the delay generator 18, and the optical modulator 54. The probe light source 12 is a photonic crystal fiber pumped by a first beam portion of the main light beam generated by the main laser 51. The probe light source 12 is adapted to be focused to areas as small as several square microns. It is understood that the probe light source 12 may be any conventional probe light source that is adapted to be focused to areas as small as several square microns such as a Q-switched sub-nanosecond microchip pulsed laser coupled to a photonic fiber, for example.

The pump light source 14 is the second beam portion of the beam from the main laser 51 adapted to produce a collimated beam with an energy level of at least several nanojoules and referred to as an excitation light source. The pump light source 14 may also be an amplified femtosecond laser, a picosecond laser, a Q-switched nanosecond laser, a dye laser, a nitrogen laser, a nanosecond microchip laser, a femtosecond laser oscillator, a harmonics generator, or an optical parametric oscillator, as desired.

The delay generator 18 is an optical delay line or an optical delay generator. The delay generator 18 is in electrical communication with the computer 23 and adapted to optically control the time delay between the probe beam produced by the probe light source 12 and the pump beam produced by the pump light source 14. The delay generator 18 is further adapted to selectively vary the delay between the pump beam and the probe beam by any amount, though typical LFP experimentation rarely requires a delay of over 10 nanoseconds.

The LFP system 10 further includes the beam splitter 52 and the reflective optic 53. The main beam generated by the main laser source 51 impinges on the beam splitter 52 and is split into two portions. The first portion beam is passed to the probe light source 12. The second portion of the main laser source beam is directed to the reflective optic 53 to redirect the second portion beam to the delay generator 18.

In use, the system 10, by varying the timing of the probe beam and pulse beam with the delay generator 18, varies the delay between the pulses available for experimentation on a sample 20 as desired, though typically the interval for experimentation will be less than ten nanoseconds.

From the foregoing description, one ordinarily skilled in the art can easily ascertain the essential characteristics of this invention and, without departing from the spirit and scope thereof, can make various changes and modifications to the invention to adapt it to various usages and conditions in accordance with the scope of the appended claims.

What is claimed is:

1. A system for flash photolysis comprising:
a main laser source for generating a beam of light;
a beam splitter for generating a first beam portion and a second beam portion from the beam of light;
a probe light source responsive to the first beam portion for generating a pulsed probe beam of light to travel through a sample in a flash photolysis application, wherein the probe light source is a laser energized photonic crystal fiber;
a pump light source responsive to the second beam portion for generating a pulsed pump beam of light to travel through the sample and initiate a chemical reaction in the sample;
a delay generator to regulate a time delay between generation of the pulsed probe beam and generation of the pulsed pump beam throughout the flash photolysis application; and
a detector to receive the pulsed probe beam exiting the sample to detect a change in absorption of the pulsed probe beam in the sample caused by the pulsed pump beam.

2. The system for flash photolysis according to claim 1 further including an optical modulator between said beam splitter and said delay generator for modulating the pulsed pump beam.

3. The system for flash photolysis according to claim 2 wherein said optical modulator is operated to block some of the pump pulses to obtain a spectrum of the probe beam pulse traveling through the sample when unpumped.

4. The system for flash photolysis according to claim 3 wherein said optical modulator is operated to block the pump pulses at a rate of every other one of the probe beam pulses to obtain a spectrum of the probe beam pulse traveling through the sample when unpumped.

5. The system for flash photolysis according to claim 2 wherein said optical modulator is operated to pass through some of the pump pulses to obtain a spectrum of the probe beam pulse traveling through the sample when pumped.

6. The system for flash photolysis according to claim 5 wherein said optical modulator is operated to pass the pump pulses at a rate of every other one of the probe beam pulses to obtain a spectrum of the probe beam pulse traveling through the sample when pumped.

7. The system for flash photolysis according to claim 1 wherein said delay generator is one of an optical delay line or an optical delay generator.

8. A system for flash photolysis comprising:
a main laser source for generating a main beam of light;
a beam splitter for generating a first beam portion and a second beam portion from the main beam of light;
a probe light source responsive to the first beam portion for generating a pulsed probe beam of light to travel through a sample in a flash photolysis application, wherein the probe light source is a laser energized photonic crystal fiber;
a pump light source responsive to the second beam portion beam for generating a pulsed pump beam of light to travel through the sample and initiate a chemical reaction in the sample;
a delay generator being one of an optical delay line and an optical delay generator to regulate a time delay between generation of the pulsed probe beam and generation of the pulsed pump beam throughout the flash photolysis application; and
a detector to receive the pulsed probe beam exiting the sample to detect a change in absorption of the pulsed probe beam in the sample caused by the pulsed pump beam.

* * * * *